US00PP26000P3

(12) United States Plant Patent
Ranney

(10) Patent No.: US PP26,000 P3
(45) Date of Patent: Oct. 20, 2015

(54) BEAUTYBERRY PLANT NAMED 'NCCX1'

(50) Latin Name: ***Callicarpa* sp.**
Varietal Denomination: NCCX1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 182 days.

(21) Appl. No.: 13/987,427

(22) Filed: Jul. 24, 2013

(65) Prior Publication Data

US 2015/0033424 P1 Jan. 29, 2015

(51) Int. Cl.
*A01H 5/02* (2006.01)

(52) U.S. Cl.
USPC ..... Plt./226

(58) Field of Classification Search
USPC ..... Plt./226
See application file for complete search history.

(56) References Cited

PUBLICATIONS

JC Ralston Arboretum at North Carolina State University, retrieved on Mar. 12, 2015, retrieved from the Internet at <http://jcra.ncsu.edu/horticulture/our-plants/results.php?search=Callicarpa> pp. 1, 36-41.*
Heavrin 2013 Michigan Gadening Magazine, retrieved on Mar. 12, 2015, retrieved from the Internet at <http://statebystategardening.com/state.php/mi/print/beautyberry/> pp. 1-2.*
Flowering Shrubs, Spring Meadow Nursery, Inc. Starter Plants Catalog and Shrub Reference 2012-2013, Sep. 12, 2012, pp. 1,2,10,27-28.*
Upov Pluto Plant Variety Database 20150306, retrieved on Mar. 9, 2015, retrieved from the Internet at <https://www.3.wipo.int/pluto/user/en/index.jsp> one page.*
Flowering Shrubs, Spring Meadow Nursery, Inc. Starter Plants Catalog and Shrub Reference 2012-2013; Sep. 12, 2012, pp. 1, 2, 10, 27 and 28.
United States Postal Service Bulk Mailing Sheet for 2012/2013 Spring Meadows Nursery Catalogue (Sep. 7, 2012).
Plant Breeders' Rights Application filed in Canada on Sep. 12, 2012.
* cited by examiner

*Primary Examiner* — June Hwu
(74) *Attorney, Agent, or Firm* — Myers Bigel Sibley & Sajovec, PA

(57) ABSTRACT

NCCX1' is a new beautyberry plant particularly distinguished by an upright rounded habit, pink/purple flower color (RHS 75A), purple young shoots and emerging leaves, long peduncles and abundant purple fruit.

2 Drawing Sheets

Latin name of the genus and species: The Latin name of the novel plant variety disclosed herein is *Callicarpa* sp.

Variety denomination: The inventive variety of *Callicarpa* sp. disclosed herein has been given the varietal denomination 'NCCX1'.

BACKGROUND OF THE INVENTION

The present invention comprises a new and distinct variety of *Callicarpa*, botanically known as *Callicarpa* sp. and hereinafter referred to by the variety name 'NCCX1'. 'NCCX1' was developed and selected in Mills River, N.C. 'NCCX1' is an open-pollinated seedling from *Callicarpa kwangtungensis*, NCSU 2005-249, (unpatented) planted adjacent to *Callicarpa dichotoma,* NCSU 2004-024, (unpatented) and appears to be an interspecific hybrid between those two species based on intermediate morphological characters. The first asexual propagation of 'NCCX1' was carried out in June 2008 by rooting stem cuttings in Mills River, N.C. and has been asexually reproduced repeatedly by vegetative cuttings in North Carolina over a four year period.

*Callicarpa* sp. 'NCCX1' roots readily from softwood cuttings treated with a basal dip of 4,000 ppm indole butyric acid (potassium salt) in water. 'NCCX1' has been found to retain its distinctive characteristics through successive asexual propagations via vegetative cuttings.

SUMMARY OF THE INVENTION

The following are the unique and distinguishing characteristics of this new cultivar when grown under normal horticultural practices in Mills River, N.C.

1. Pink/purple flowers with an average of 40 flowers per inflorescence.
2. Purple young shoots and emerging leaves.
3. Abundant purple fruit with long peduncles.

BRIEF DESCRIPTION OF THE DRAWINGS

This new beautyberry variety is illustrated by the accompanying photographs which show the plant's form, foliage, flowers and fruit. The colors shown are as true as can be reasonably obtained by conventional photographic procedures. Colors in the photographs may differ slightly from the color values cited in the detailed botanical description, which accurately describe the colors of the new *Callicarpa* sp. variety. The photographs were taken in Mills River, N.C.

DETAILED BOTANICAL DESCRIPTION

Figure 1:
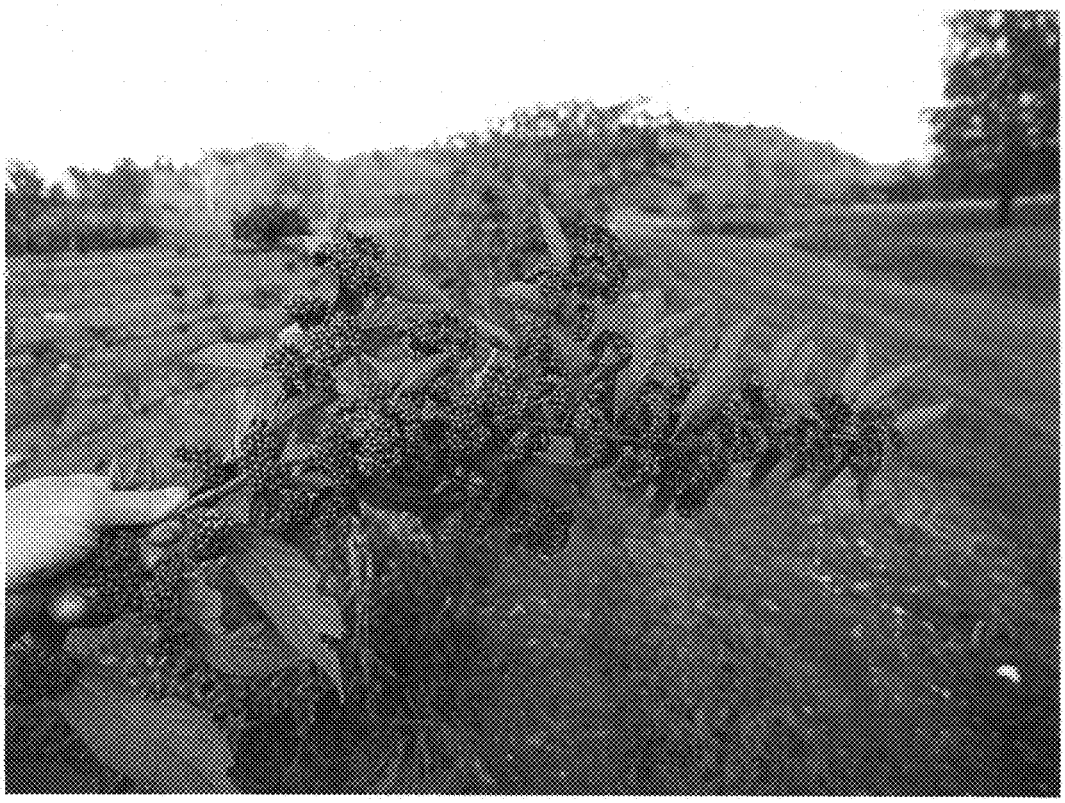
FIG. 1 is a color photograph of fruit on a mature three year old plant, taken on Oct. 26, 2010.
Figure 2:
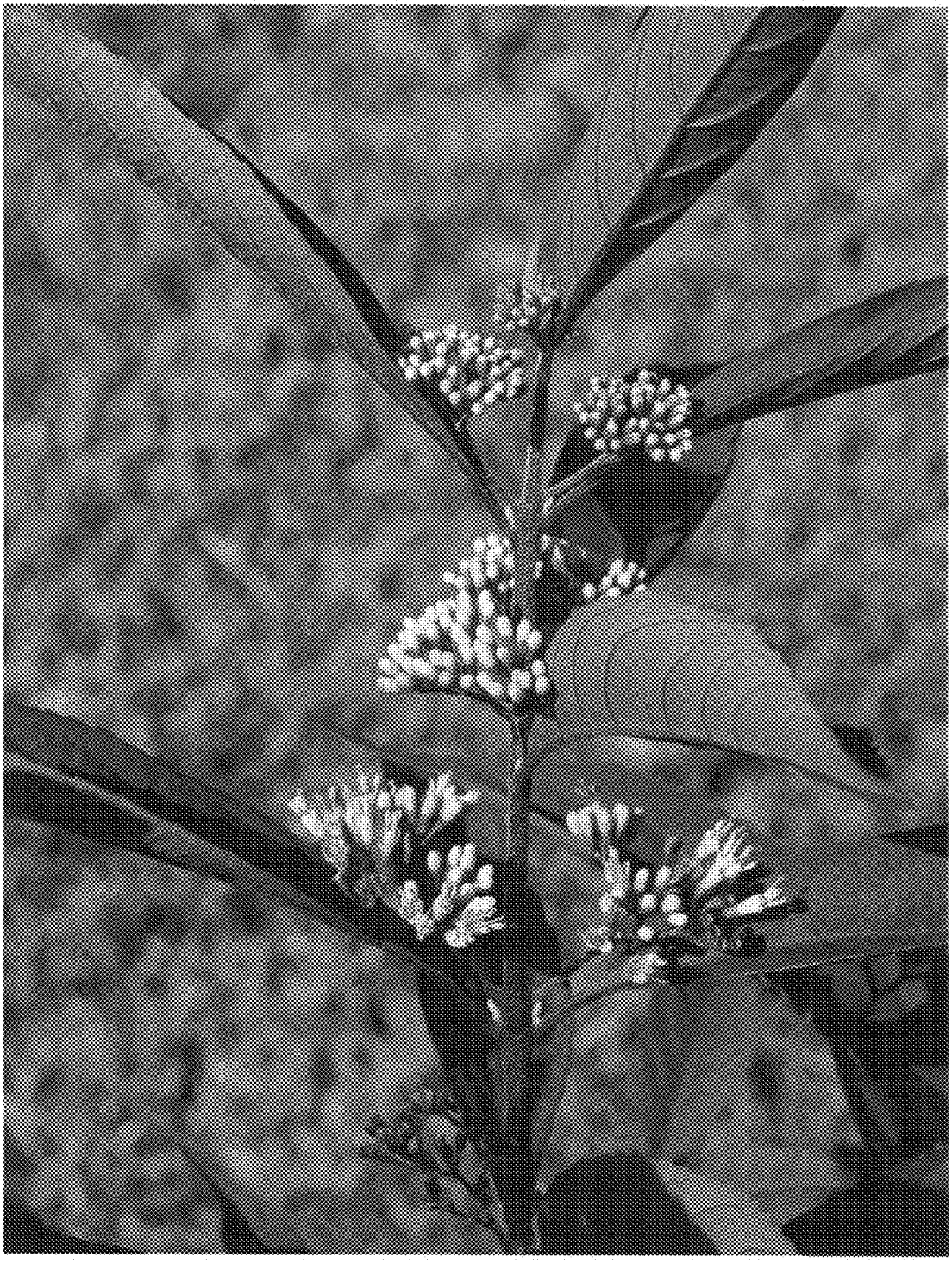
FIG. 2 is a color photograph of the flowers on a mature three year old plant, taken on Sep. 29, 2009.

The following is a detailed description of the botanical characteristics of the new and distinct variety of *Callicarpa* sp. plant known by the denomination 'NCCX1'. The detailed description was taken on five-year-old plants growing under landscape conditions in Mills River, N.C. in June 2012. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Technical Description of the Variety.

Classification:

*Botanical name.*—*Callicarpa* sp.

*Common name.*—Beautyberry.

*Denomination.*—'NCCX1'.

Parentage: Open-pollinated seedling from *Callicarpa kwangtungensis* (NCSU 2005-249).

Plant description:

*Growth habit.*—Upright rounded.

*Plant shape.*—Rounded.

*Height at maturity.*—2 meters to 2.5 meters.

*Width at maturity.*—2 meters to 2.5 meters.

Shoot:

*Mature shoot texture.*—Slightly pubescent.

*Mature shoot color.*—Closest to RHS 201A (Grey).

*Immature shoot texture.*—Pubescent with stellate hairs, especially near tip.

*Immature shoot color.*—RHS N77A (Purple).

Stem:

*Shape.*—Round in cross section.

*Surface texture.*—Glaborous.

*Color.*—Grey-green RHS 197C to grey-brown RHS199D.

Leaves:

*Type.*—Simple.

*Arrangement.*—Opposite.

*Shape.*—Elliptic to ovate-lanceolate.

*Apex.*—Long acuminate.

*Base.*—Cuneate.

*Veins.*—Type: Pinnate. Adaxial & abaxial vein color: Closest to RHS 59B (Red-Purple). Surface texture: Pubescent.

*Margin.*—Serrate above middle.

*Mature leaf size.*—Length: Average is 9.8 cm (range is 6.7 cm to 10.2 cm). Width at widest: Average is 2.9 cm (range is 2.6 cm to 3.1 cm).

*Immature leaf color.*—Adaxial (upper) surface: Closest to RHS N77A (Purple). Abaxial (lower) surface: Closest to RHS 148A (Yellow-Green).

*Immature Leaf texture.*—Adaxial surface texture: Pubescent. Abaxial surface texture: Pubescent.

*Mature leaf color.*—Adaxial (upper) surface: Closest to RHS 147A (Yellow-Green). Abaxial (lower) surface: RHS 147B (Yellow-Green). Texture: Adaxial: Sparsely pubescent with glandular hairs. Abaxial: Sparsely pubescent with glandular hairs. Fall color: Variable, with shades of RHS 186A (Greyed Purple), RHS 22A (Yellow-Orange), and RHS 168A (Greyed-Orange). Leaf attachment: Petiolate. Petiole: Shape: Semi-terete. Length: Average is 0.7 cm (range is 0.3 cm to 0.8 cm). Width: Average is 0.155 cm (range is 0.105 cm to 0.207 cm). Surface: Sparsely pubescent.

Inflorescence:

*Inflorescence type.*—Cyme.

*Inflorescence diameter.*—Average is 3.4 cm (range is 2 cm to 4.6 cm).

*Inflorescence length.*—Average is 3.4 cm (range is 2.2 cm to 4.2 cm).

*Number of flowers per inflorescence.*—Average is 40 (range is 11 to 88).

*Flowering season.*—Beginning in June and lasting until October in Mills River, N.C.

*Lastingness of flower on the plant.*—Begins June 14 till late Fall or Early-Winter; Individual flowers persist for 1 to 3 days and bloom in sequence from the base of the shoot tip to the tip over a period from mid-June to late Fall.

*Fragrance.*—No significant fragrance observed.

*Self cleaning or persistent.*—Self cleaning.

*Bud.*—Bud shape: Oblong-oval. Bud diameter at balloon stage: Average 0.146 cm (range is 0.142 cm to 0.154 cm). Bud length at balloon stage: Average 0.447 cm (range is 0.427 cm to 0.47 cm). Bud color: RHS 75C (Purple).

*Perianth.*—Diameter at antithesis: Average 0.425 cm (range is 0.306 cm to 0.552 cm).

*Petal.*—Number of petals per flower: 4. Color, adaxial (upper) surface at anthesis: RHS 75A (Purple). Color, abaxial (lower) surfaces at anthesis: Ranging between RHS 75A (Purple) and RHS 75B (Purple). Surface texture and appearance: Glabrous. Shape: Campanulate flower form. Apex: Acute. Base: Petals fused together at base. Margin: Entire above fused region. Length: Average is 0.461 cm (range is 0.454 cm to 0.484 cm). Width: Average is 0.155 cm (range is 0.132 cm to 0.177 cm). Petals, fused or unfused: Fused.

*Peduncle.*—Color: RHS N77A (Purple). Length: Average 1.6 cm (range is 1 cm to 2.6 cm). Width: Average 0.087 cm (range is 0.066 cm to 0.106 cm). Shape: Cylindrical to semi-terete. Surface texture: Pubescent with stellate hairs.

*Bract.*—Number: 2 to 12 (or more) per inflorescence. Length: Average 0.2 cm (range is 0.1 cm to 0.7 cm). Width: Average 0.052 cm (range is 0.033 cm to 0.111 cm) Color: RHS N77A (Purple).

*Sepals.*—Number: 4. Color: RHS N77A (Purple). Surface texture: Sparsely glandular. Shape: Funnel form. Apex: Abruptly acute. Base: Fused. Margin: Entire above fused region. Length: Average 0.242 cm (range is 0.210 cm to 0.264 cm). Width: Average 0.111 cm (range is 0.10 cm to 0.123 cm).

Reproductive organs:

*Stamen.*—Quantity per flower: 4. Shape: Oblong elliptic, exerted beyond petals. Filament color at anthesis: Translucent RHS 155A (White). Length: Average is 0.496 cm (range is 0.471 cm to 0.534 cm). Width of filament: Average 0.0069 cm (range is 0.0048 cm to 0.010 cm).

*Anther.*—Length: Average is 0.183 cm (range is 0.167 cm to 0.205 cm). Width at widest: Average is 0.0724 cm (range is 0.032 cm to 0.102 cm). Dehiscence: Poricidal; dehiscing through a pore-like opening at the apex. Color: RHS 9C (Yellow). Pollen color: RHS 9C (Yellow). Attachment: dorsifixed.

*Pistil.*—Length: Average 0.742 cm (range 0.682 cm to 0.806 cm). Style Length: Average 0.6 cm (range 0.529 cm to 0.64 cm). Style Width at midpoint: Average 0.023 cm (range is 0.015 cm to 0.029 cm). Ovary: Superior.

Fruit/seed set:

*Fruit*.—Color: Purple RHS N78A to purple-violet RHS N81 to N82. Shape: globose. Surface texture: glabrous, shiny, glossy. Size: Average is 0.498 cm (range is 0.439 cm to 0.521 cm). Amount of fruit set: very abundant. Amount of fruit per cluster: Average 4, but range from 0 to 80.

*Seed*.—Color: RHS 18B (Yellow-orange). Shape: ovoid, flattened. Length: Average is 0.115 cm (range is 0.08 cm to 0.135 cm). Width: Average is 0.059 cm (range is 0.047 to 0.08 cm). Surface texture: Glabrous.

Disease and insect resistance: No significant disease or insect pests have been observed.

Comparison with Parental Lines and Known Varieties

*Callicarpa* sp. 'NCCX1' is distinguished from the female parent *Callicarpa kwantungensis* NCSU 2005-249 (unpatented) in that 'NCCX1' has an upright rounded habit, pink/purple flower color (RHS 75A), more flowers per inflorescence (average of 40), longer peduncles (average length of 1.6 cm) and more abundant, larger (average diameter of 0.5 cm), purple (RHS N78A) fruit, while *C. kwantungensis* has a narrow upright habit, white flowers (RHS 155B), shorter peduncles (average length of 0.25 cm), and smaller (average diameter of 0.37 cm), less abundant, purple-violet (RHS N80A) fruit.

Table 1 shows the specific comparisons of *Callicarpa* sp. 'NCCX1' to *Callicarpa bodinieri* var. *giraldii* 'Profusion' NCSU 2001-064, *Callicarpa kwantungensis* NCSU 2005-249, and *Callicarpa dichotoma* 'Issai' NCSU 2006-024.

TABLE 1

Comparison of *Callicarpa* sp. 'NCCX1' with other *Callicarpa* taxa.

| | *Callicarpa* 'NCCX1' | *Callicarpa bodinieri* 'Profusion' |
|---|---|---|
| Habit | full, rounded and upright | upright and open |
| Shoot color | dark purple new shoots (RHS N77A) | dark gray (RHS 197A); no significant purple color on new shoots |
| Leaf color | emerging leaves purple (RHS N77A); expanded leaves green (RHS 147A) | both emerging and mature leaves are medium green (RHS 144A) to deep green (RHS 147A) |
| Leaf venation | purple mid-rib (RHS 59B) extends about 46% of length from lamina base to tip | purple mid-rib (RHS N77A) extends about 12% of length from lamina base to tip |
| Petiole | dark purple (RHS N77A); average length 0.7 cm (range 0.3 to 0.8 cm) | dark purple (RHS N77A); average length 1.48 cm (range 0.8 to 2.1 cm) |
| Flowering time in Mills River, NC | mid June | late May |
| Flowers per inflorescence | Average 40 (range is 11 to 88) | Average 17 (range is 4 to 32) |
| Flower color | pink/purple (RHS 75A) | medium purple-pink (RHS N78A) |

TABLE 1-continued

Comparison of *Callicarpa* sp. 'NCCX1' with other *Callicarpa* taxa.

| | | |
|---|---|---|
| Flower position | on long peduncles; not held in ranks | short peduncles; cymes well-branched with fruit encircling shoot |
| Peduncle length | Average 1.6 cm (range is 1 to 2.6 cm) | Average 0.548 cm (range is 0.369 to 0.962 cm) |
| Fruit abundance | very abundant | abundant |
| Fruit color | vibrant purple (RHS N78A) | red-purple (RHS 72A) |
| Fruit size | 0.5 cm average per drupe | 0.48 cm average per drupe |
| Maturity of fruit | beginning to ripen in late August, peak fruit color in late September to frost | beginning to ripen in August, peak fruit color in September to frost |
| | *Callicarpa kwangtungensis* | *Callicarpa dichototna* 'Issai' |
| Habit | narrow upright; stiff straight stems | dense upright |
| Shoot color | gray-brown (RHS 199A); no significant purple color on new shoots | dark purple new shoots (RHS N77A) |
| Leaf color | emerging leaves purple (RHS N79A-N77A); mature leaves overall dull olive green (RHS 152A) | both emerging and mature leaves green (RHS 146B) |
| Leaf venation | purple mid-rib (RHS N77A) extends 100% from lamina base to tip | purple mid-rib (RHS N77A) extends about 8% from lamina base to tip |
| Petiole | dark purple (RHS N77A); average length 1.15 cm (range 0.8 to 1.5 cm) | dark purple (RHS N77A); average length 0.49 cm (range 0.3 to 0.6 cm) |
| Flowering time in Mills River, NC | late June | mid June |
| Flowers per inflorescence | Average 17 (range is 12 to 27) | Average 15 (range is 12 to 25) |
| Flower color | white (RHS 155B) | pale purple-pink (closest to RHS 75A) |
| Flower position | short peduncles clustered and hidden in leaf axil | held proud from foliage in ranks along shoot |
| Peduncle length | Average 0.252 cm (range is 0.201 to 0.315 cm) | Average 0.591 cm (range is 0.455 to 0.72 cm) |
| Fruit abundance | minimal | very abundant |
| Fruit color | purple-violet (RHS N80A) | vibrant purple (RHS N81A) |
| Fruit size | 0.37 cm average per drupe | 0.34 cm average per drupe |
| Maturity of fruit | beginning to ripen in September, peak fruit color in late September to frost | beginning to ripen in August, peak fruit color in mid September to frost |

What is claimed is:

1. A new and distinct variety of beautyberry plant named 'NCCX1,' substantially as illustrated and described herein.

* * * * *